United States Patent
Schmieding et al.

(10) Patent No.: US 8,177,738 B2
(45) Date of Patent: May 15, 2012

(54) BONE VOID FILLING TUBE AND SHEAR MECHANISM

(75) Inventors: Reinhold Schmieding, Naples, FL (US); Robert Benedict, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 12/840,931

(22) Filed: Jul. 21, 2010

(65) Prior Publication Data

US 2011/0028903 A1 Feb. 3, 2011

Related U.S. Application Data

(60) Provisional application No. 61/229,159, filed on Jul. 28, 2009.

(51) Int. Cl.
*A61M 31/00* (2006.01)
*A61M 5/00* (2006.01)
*A61M 5/315* (2006.01)

(52) U.S. Cl. ............. 604/60; 604/59; 604/187; 604/218

(58) Field of Classification Search .............. 604/15–18, 604/38, 311, 207, 218–240, 170, 174, 167, 604/264, 57, 59, 60, 93.01, 137, 151, 181, 604/187, 200, 246; 606/167, 170, 174, 151, 606/200

See application file for complete search history.

(56) References Cited

U.S. PATENT DOCUMENTS

| | | | | | |
|---|---|---|---|---|---|
| 682,090 | A | * | 9/1901 | Lee | 604/13 |
| 4,790,819 | A | * | 12/1988 | Li et al. | 604/59 |
| 6,090,063 | A | * | 7/2000 | Makower et al. | 604/13 |
| 2004/0037819 | A1 | * | 2/2004 | Pascher et al. | 424/93.21 |
| 2005/0175703 | A1 | * | 8/2005 | Hunter et al. | 424/486 |

* cited by examiner

*Primary Examiner* — Jackie Ho
*Assistant Examiner* — Leah Stohr
(74) *Attorney, Agent, or Firm* — Dickstein Shapiro LLP

(57) ABSTRACT

Apparatus and methods for delivering a clotted biological component (such as blood, autologous conditioned plasma (ACP), platelet-rich plasma (PRP), bone marrow aspirate (BMA), demineralized bone matrix, anticoagulants and/or clotting agents, or combination of these materials) into a tissue void (for example, a bone void such as a bone tunnel, socket, opening or cavity), and then cutting the clotted biological component with a cutting or shearing mechanism at the tissue surface. The apparatus is provided with a tube and a cutting or shearing mechanism (provided on or within the distal end of the tube) that is actuated to cut or break off the clot at the desired insertion length. The tube may then be placed over the next tissue void so that the obturator drives the next clot into the next tissue void until all tissue voids are filled. Upon insertion at the defect site, the biological component advances the healing of the damaged tissue and tissue growth.

18 Claims, 3 Drawing Sheets

BONE VOID FILLING TUBE AND SHEAR MECHANISM

CROSS-REFERENCE TO RELATED APPLICATIONS

This application claims the benefit of U.S. Provisional Application No. 61/229,159, filed Jul. 28, 2009, the entire disclosure of which is incorporated by reference herein.

FIELD OF THE INVENTION

The present invention relates to the delivery of a biological clot to a tissue void such as a bone void.

BACKGROUND OF THE INVENTION

Joint injuries typically involve damage to the bones and/or tendons that form the joint. This damage can range from bone chips to tears to simple wear. In the case of bone chips or wear, it is often necessary to repair the damage by replacing the missing bone material. This has been typically accomplished by attaching an implant over the defect that replicates the original bone structure. It is often necessary to also fill out the bone void formed in the bone structure (i.e., a transosseous tunnel or socket at the defect site, or an OATS harvesting site) with biological materials such as blood and/or growth factors, to facilitate wound healing.

BRIEF SUMMARY OF THE INVENTION

The present invention relates to methods and apparatus for delivering a clot (formed of blood, autologous conditioned plasma (ACP), platelet-rich plasma (PRP), bone marrow aspirate (BMA), demineralized bone matrix, anticoagulants and/or clotting agents, growth factors, or combination of these materials) into a tissue void (for example, a bone void such as a bone tunnel, socket, opening or cavity), and then cutting the clot with a cutting or shearing mechanism at the tissue surface.

The void filling apparatus of the present invention is provided with a tube having a shearing mechanism configured to cut or break off the clot (delivered through the tube) at the tissue surface in a precise manner. The cutting mechanism may be (i) a single blade; (ii) a double blade that acts in a "sickle" motion; (iii) a flat blade that rotates outside the inner diameter of the tube to allow the clot to advance and then swings inwards to cleave the clot; or (iv) a mechanism which is not intrinsic to the tube, such as a mechanism similar to a cigar cutter.

The present invention also provides a method of treatment of tissue (such as bone or other anatomical tissue) by: (i) providing a clot of biological component (such as blood, autologous conditioned plasma (ACP), platelet-rich plasma (PRP), bone marrow aspirate (BMA), demineralized bone matrix, anticoagulants and/or clotting agents, growth factors, or combination of these materials) in the proximity of a tissue void (for example, a bone void); (ii) delivering the clot into the tissue void; and (iii) cutting the clot, at the tissue surface, once the desired volume of the tissue void has been filled by at least part of the clot.

Other features and advantages of the present invention will become apparent from the following description of the invention, which refers to the accompanying drawings.

DETAILED DESCRIPTION OF THE INVENTION

Figure 1:
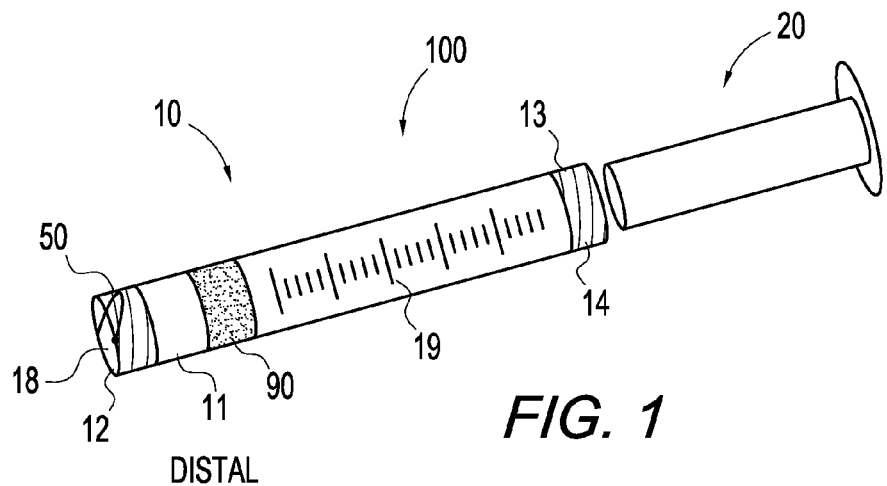
FIG. 1 illustrates an apparatus for delivering and cutting a clot of biological component in accordance with an embodiment of the present invention.
Figure 2:
FIGS. 2(a)-(b) illustrate various proximal caps of the tube of the apparatus of FIG. 1.
Figure 2:
Figure 3:
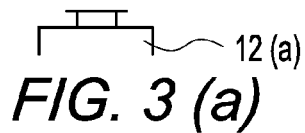
FIGS. 3(a)-(b) illustrate various distal caps of the tube of the apparatus of FIG. 1.
Figure 3:
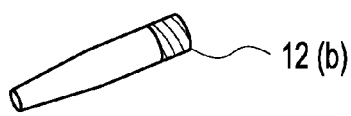
Figure 4:
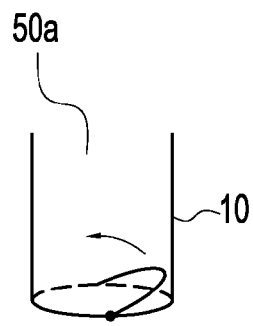
FIGS. 4(a)-(e) illustrate various views of the cutting mechanism of the tube of the apparatus of FIG. 1.
Figure 4:
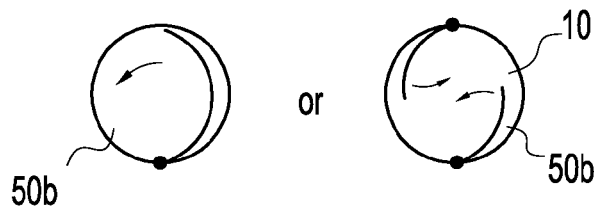
Figure 4:
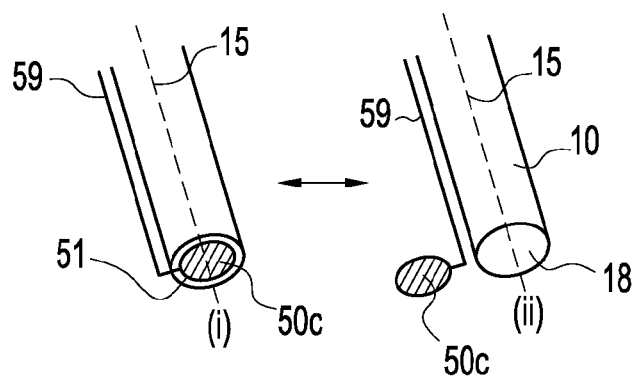
Figure 4:
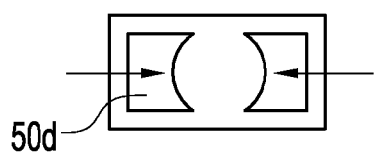
Figure 4:
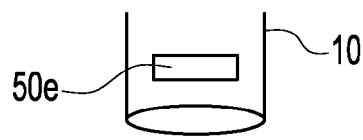

The examples provided below detail the preferred embodiments of the present invention. Other features, embodiments, and advantages of the invention beyond those discussed in the detailed description will be obvious to those skilled in the art. Those skilled in the art should appreciate that many changes may be made to the present invention without departing from the scope or spirit of the present invention.

The present invention provides methods and apparatus for delivering a clotted biological component (such as blood, autologous conditioned plasma (ACP), platelet-rich plasma (PRP), bone marrow aspirate (BMA), demineralized bone matrix, anticoagulants and/or clotting agents, growth factors, or any combination of these materials) into a tissue void (for example, a bone void such as a bone tunnel, socket, opening or cavity), and then cutting the clotted biological component with a cutting or shearing mechanism at the tissue surface (for example, the bone surface).

In an exemplary embodiment only, the tissue to be treated is bone and the tissue void is a bone void (such as a bone socket, tunnel, opening or cavity, or a void formed between two adjacent bones, such as between two vertebrae, for example). Although the apparatus and methods of the present invention will be detailed below with reference to treatment of a particular tissue void (i.e., treatment of a bone void), the invention is not limited to this exemplary embodiment only, and encompasses treatment of any void in other anatomical regions in humans and other animal bodies.

According to an exemplary embodiment only, the apparatus of the present invention comprises a tube and an obturator (with half mm inner diameter increments) designed to be received within the tube. The proximal end of the tube is provided with a proximal cap which may have various inner diameter sizes. The proximal cap may be a luer lock (to allow injection of the biological component and/or of other liquid or mixture) or a screw on cap (to allow mixing).

The distal end of the tube is provided with a distal cap which may have various inner diameter sizes. The distal cap may be a screw on cap (to allow mixing/injection of the biological component) or a screw on, tapered extension (to allow easy injection of the clotted biological component in the tube). The distal end of the tube is also provided with a cutting or shearing mechanism configured to cut or break off the clotted biological component (delivered through the tube) at the bone surface in a precise manner. The cutting mechanism may be (i) a single blade; (ii) a double blade that acts in a "sickle" motion; (iii) a flat blade that rotates outside the inner diameter of the tube to allow the clot to advance and then swings inwards to cleave the clot; or (iv) a mechanism which is not intrinsic to the tube, such as a mechanism similar to a cigar cutter.

After the formation of the clot of biological component, the distal cap of the tube is removed and the tube is placed over the predefined bone void to be filled with the biological component. The obturator is advanced so that the clot is pushed into the bone void until the clot bottoms out or the length of the clot desired is inserted. The cutting or shearing mechanism (provided on or within the distal end of the tube) is then actuated to cut or break off the clot at the desired insertion length. The tube may then be placed over the next bone void (hole) so that the obturator drives the next clot into the next bone void until all bone voids are filled. Upon insertion at the defect site, the biological component advances the healing of the damaged tissue and tissue growth.

The present invention also provides a method of repairing bone damage by: (i) providing a clot of biological component (such as blood, autologous conditioned plasma (ACP), platelet-rich plasma (PRP), bone marrow aspirate (BMA), demineralized bone matrix, anticoagulants and/or clotting agents, or any combination of these materials) in the proximity of a bone void (such as a bone tunnel or socket); (ii) delivering the clot into the bone void; and (iii) cutting the clot, at the bone surface, once the desired volume of the bone void has been filled by at least part of the clot.

Referring now to the drawings, where like elements are designated by like reference numerals, FIGS. 1-7 illustrate various views of apparatus 100 of the present invention, designed to deliver a clot of biological component into a bone void (such as a bone tunnel or socket, or bone opening or cavity), and then cutting the clot with a cutting or shearing mechanism at the bone surface. As shown in the drawings, delivery apparatus 100 comprises a tube 10 and an obturator 20 designed to be received within the tube 10 and to extend through at least a portion of a lumen 18 of the tube 10. As shown in FIG. 1, tube 10 is provided with inner diameter increments 19 (for example, half mm inner diameter increments 19). A depth gauge in mm increments may be also provided at the proximal end of the tube 10 to assist in delivery of the clot (as detailed below).

Obturator 20 may also be a plunger or rod or other similar structure which is sized and configured to slidingly pass through the interior of tube 10 (i.e., to slidingly engage with the inner wall of inner lumen 18 of the tube 10 as the obturator advances therethrough). In a preferred embodiment, the shape and size of the cross-sectional area of the tube 10 is about similar to the shape and size of the cross-sectional area of obturator 20 such that, upon advancement of the obturator relative to the tube 10, the obturator 20 is capable of displacing at least a part of clot 90 (or at least a part of clotted biological composition 90) as the obturator advances.

Tube 10 may be formed of a material such as sterile teflon or polypropylene, for example. Proximal end 13 (FIG. 1) of the tube 10 is provided with a proximal cap 14 which may have various inner diameter sizes. As illustrated in FIGS. 2(a)-(b), the proximal cap may be a luer lock 14a (to allow injection of the biological component and/or of other liquid or mixture) or a screw-on cap 14b (to allow mixing).

Distal end 11 (FIG. 1) of the tube 10 is provided with a distal cap 12 which may also have various inner diameter sizes. As illustrated in FIGS. 3(a)-(b), the distal cap may be a screw-on cap 12a (to allow mixing/injection of the biological component) or a screw-on, tapered extension 12b (to allow easy injection of the clotted biological component in the tube).

As shown in FIG. 1, distal end 11 of the tube 10 is also provided with a cutting or shearing mechanism 50 configured to cut or break off the clotted biological component 90 (delivered through the tube 10) at the bone surface in a precise manner. Preferably, cutting or shearing mechanism 50 is provided at a most distal end of the tube 10. Details of the cutting or shearing mechanism 50 are illustrated in FIGS. 4(a)-(e).

As shown in FIGS. 4(a)-(e), the cutting mechanism may be (i) a single blade 50a (FIG. 4(a)) that may be curved to fit the inner diameter of the distal end of the tube 10 and that pivots on a hinge activated by a spring, for example, or by other method at or near the proximal end; (ii) a double blade 50b (FIG. 4(b)) that acts in a "sickle" motion from single pivot points (in a manner similar to the single blade 50a); (iii) a flat blade 50c (FIG. 4(c)) that rotates outside the inner diameter of the tube to allow the clot to advance, and then swings inwards to cleave the clot; or (iv) a mechanism 50d, 50e (FIG. 4(d)) which is not intrinsic to the tube 10, such as mechanism 50d which is similar to a cigar cutter, or mechanism 50e which is a slot in the tube 10 for the blade to shear inside (the slot may be positioned so that the cap will cover the slot).

Flat blade 50c shown in FIG. 4(c) may have a generally circular configuration, with a surface area about equal to the surface area of the inner lumen of the tube 10. In an exemplary embodiment, outer surface 51 of the blade 50c is about perpendicular to longitudinal axis 15 of the tube 10 and the blade is configured to be rotated (by an actuating mechanism 59, for example) from a first or closed position (as shown in position "i") to a second or open position (as shown in position "ii"). In the closed position, the flat blade 50c blocks the inner lumen of the tube 10 preventing clot 90 from passing through and exiting the most distal end of the tube 10. In the open position, the flat blade 50c partially or fully opens the inner lumen 18 of the tube 10, allowing the clot 90 to pass therethrough for further delivery into a bone void.

The clotted biological composition 90 of the present invention may be a stable biological clot that can be delivered into a transosseous tunnel or socket, in the vicinity of the defect to be repaired, to advance the healing of the damaged tissue and tissue growth.

According to exemplary embodiments only, the biological component of the present invention comprises at least one of blood, autologous conditioned plasma (ACP), platelet-rich plasma (PRP), bone marrow aspirate (BMA), demineralized bone matrix, anticoagulants and/or clotting agents, and/or growth factors, for example.

In an exemplary embodiment only, ACP may be obtained from blood from the patient, which is separated using a centrifuge, for example, to retrieve certain healing components such as growth factors, to obtain the ACP. Preferably, the ACP has a platelet concentration factor of about 2 compared to the platelet concentration of the patient's normal blood. For example, the ACP may contain about 470,000 platelet/microliter (for a donor) compared to the about 200,000 platelet/microliter of the donor's whole blood, and compared to the about 500,000-1,000,000 platelet/microliter of the platelet-rich plasma (PRP) (of the donor), and compared to about 0 platelet/microliter of the platelet-poor plasma (PPP) (of the donor).

The ACP may also comprise anti-coagulants such as ACD-A, for example, and/or clotting agents, such as thrombin, for example, to control the clotting time. The ACP may further comprise demineralized bone matrix (DBM) or other bone void filler materials to enhance the biological and/or structural components of the substrate.

The ACP may also comprise autologous growth factors as defined below. In a preferred embodiment, the term "growth factor" includes autologous growth factors produced from a patient's own blood, obtained by a centrifugation process. Optionally, the ACP may comprise additional antiseptic chemicals and/or antibiotics and/or electrolytes. The additional antiseptics and/or the antibiotics and/or the electrolytes will typically be present in the plasma in a predetermined concentration range, which will be dependent upon the particular tissue site and application, as well as the specific activity of the antiseptic and/or the antibiotic and/or the electrolytes. The antibiotics may be selected from the group consisting of a neosporin, vancomycin and gentamycin, and combinations thereof.

The ACP may further comprise one or more additional components which promote or enhance the wound healing effectiveness of the autologous growth factors. As such, hormones or site-specific hybrid proteins may be incorporated in the autologous blood suspension to maximize the availability of the autologous growth factors at the tissue to be repaired and/or to potentiate wound healing.

Growth factors may comprise proteinaceous factors, for example, which play a role in the induction or conduction of growth of tissue, ligaments, bone, cartilage or other tissues associated with bone or joints. In particular, the following growth factors contained in platelets are set forth below (and their effects):

PDGF (Platelet-derived growth factor)—Stimulates collagen synthesis, the formation of blood vessels and fibroblast proliferation; activation of macrophages and neutrophiles; activates TGF-β; attracts stem cells.

FGF (Fibroblast growth factor)—Stimulates the formation of blood vessels, collagen synthesis, wound contraction, matrix synthesis, epithelialisation.

TGF-β (Transforming growth factor β)—Reduces scar formation; reduces wound healing disturbances caused by corticoids; attracts fibroblasts and promotes their proliferation; stimulates collagen synthesis; promotes the secretion of FGF and PDGF by monocytes.

TGF-α (Transforming growth factor-α)—Stimulates mesenchymal, epithelial and endothelial cells.

EGF—(Epithelial Growth Factor)—Stimulates re-epithelialisation, the formation of new blood vessels and collagenase activity.

A method of delivering the clotted biological composition 90 of the present invention into a bone void (such as a bone tunnel or socket), and then cutting the clotted biological component with the apparatus of the present invention, begins by forming the clot of biological material. For this, the distal end 11 of the tube 10 is capped (by employing distal cap 12a, for example) and then the autologous conditioned plasma (ACP) (by itself or in combination with other components such as blood, bone marrow aspirate, etc., as detailed above) are injected through the proximal end 13 (for example, through proximal cap 14a). Anti-coagulants (e.g., ACD-A) and/or clotting agents (e.g., thrombin) and/or additional filler materials such as demineralized bone matrix (DBM) or other bone void filler materials may be added to enhance the biological and/or structural components of the substrate, and mixed with the autologous conditioned plasma (ACP).

After mixing, the distal cap 12a of the tube 10 is removed, and the tube 10 is placed over the predefined bone void to be filled with the clot 90. The obturator 20 is advanced so that the clot 90 is pushed into the bone void until the clot bottoms out or the length of the clot desired is inserted. The cutting or shearing mechanism 50 (provided on or within the distal end of the tube) is then actuated to cut or break off the clot at the desired insertion length. The tube 10 may then be placed over the next bone void (hole) so that the obturator 20 drives the next clot into the next bone void until all bone voids are filled. Upon insertion at the defect site, the biological component advances the healing of the damaged tissue and tissue growth.

In another embodiment, a matrix or structural material (such as a suture, tape, or a porous material such as a collagen matrix) may be placed within at least a length of the tube 10, to allow the clot formation on the material of matrix. Alternatively, the formation of the clot may occur within the material of the matrix (for example, within the pores of a porous matrix).

Figure 5:
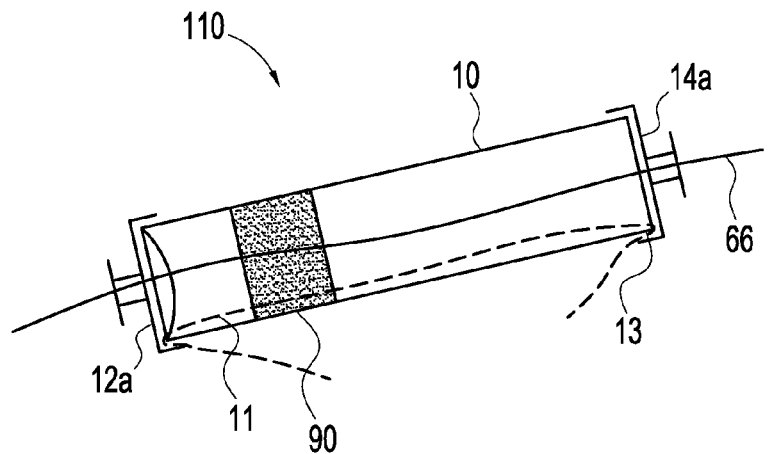
FIG. 5 illustrates a tube of an apparatus for delivering and cutting a clot of biological component, in accordance with another embodiment of the present invention (with a suture strand extending through the tube and secured to the tube)

FIG. 5 illustrates tube 10 of an apparatus 110 for delivering and cutting a clot 90 of biological component in accordance with the embodiment described in the paragraph above. According to this exemplary embodiment only, at least one material strand 66 (for example, a flexible suture strand 66 or a suture tape 66) is placed within at least a portion of the tube 10, to allow the formation of the clot 90 on the material or matrix 66, making it available for transport and placement for other indications. If desired, a plurality of flexible strands 66 may be provided within at least a length of the inner lumen 18 of the tube 10, to allow formation of the clot on, or within, the plurality of flexible strands 66.

Figure 6:
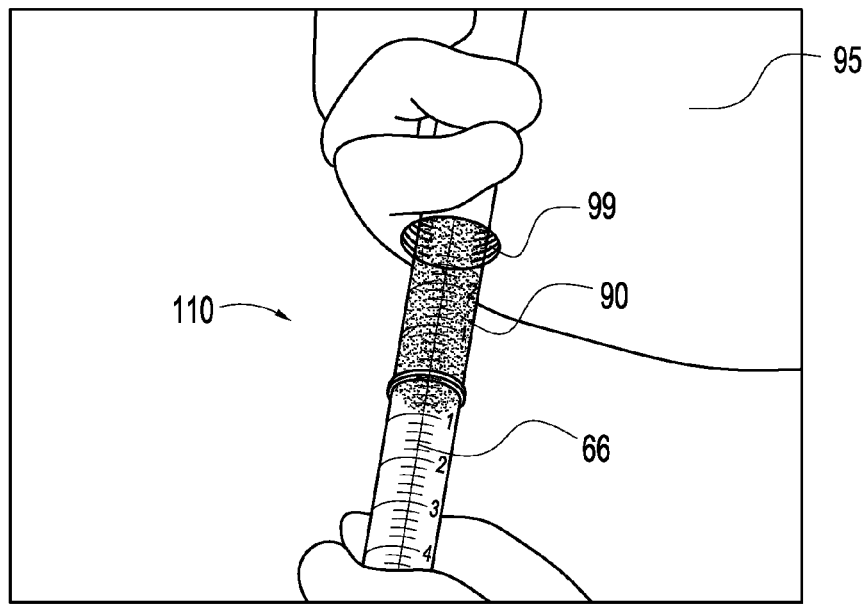
FIG. 6 illustrates another view of the apparatus of FIG. 5 in the proximity of a surgical site and undergoing a bone void filling operation according to a method of the present invention (with syringe-to-syringe transfer of ACP, mimicking BVF tube design)

Caps may be designed to ensure that the matrix 66 (i.e., suture strand 66) is centered in the tube 10. The strand 66 may pass through the caps, and may be held by the caps (at the edge of the tube 10, for example). The strand 66 helps in guiding the clot 90 through the bone tunnel 99 (FIG. 6). In lieu of the strand, any absorbant material or matrix construct may be used, to guide the clot and deliver the clot at the desired location.

Figure 7:
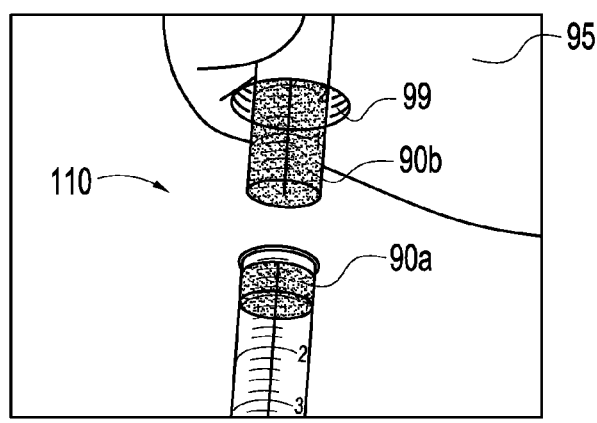
FIG. 7 illustrates the apparatus of FIG. 6 at a stage of bone void filling subsequent to that shown in FIG. 6 (with the clot already cut with the cutting mechanism of the apparatus of FIG. 6).

FIG. 6 illustrates delivery apparatus 110 of the present invention (shown in FIG. 5) in the proximity of a surgical site 99 (i.e., a bone tunnel 99 formed within bone 95) and undergoing a bone void filling operation according to a method of the present invention (with syringe-to-syringe transfer of ACP, mimicking BVF tube design). FIG. 7 illustrates clot 90 already cut or sheared with the blade of the cutting mechanism 50 of the apparatus 110 of FIG. 6, with first clot part 90a remaining within the tube 10 and with second clot part 90b filling the bone tunnel 99. The second clot part 90b may partially or fully fill the bone tunnel 99.

The clotted biological component of the present invention may be used for filling bone voids in various applications, for example, filling bone tunnels or sockets in ACL reconstructions, OATS harvesting sites, bone screw home sites, ACL/PCL tunnels, arthroscopic knee resurfacing, hip resurfacing, patella resurfacing, OATS resurfacing, among many other arthroscopic applications.

The clot of the present invention may also comprise other stabilizing, therapeutic and/or filling materials such as collagen or a flowable material, such as bone cement, allograft tissue, autograft tissue, hydroxyapatite or other natural or synthetic bone substitute, which can be added to the clot and introduced into the tissue void and which, in time, allows setting to a more-hardened condition. If desired, these additional materials (such as bone cement, allograft tissue, autograft tissue, hydroxyapatite, etc.) may be introduced into the bone void (or placed at the surface of the tissue adjacent the void) and subsequent to the filling of the void with the clot, to "seal" the clot at the surgical site.

If desired, the clot may also comprise a compression-resistant material, such as rubber, polyurethane, cyanoacrylate, or silicone rubber, or a semi-solid slurry material (e.g., a bone slurry in a saline base), which is either contained within the clot or adheres to the matrix 66 (i.e., strand 66). The clot may further comprise medication, or a combination of medication and compression-resistant material, as described above.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A device for filling a tissue void in a patient, comprising:
   a tube having an inner lumen configured to house a clotted biological component;
   the clotted biological component housed within the inner lumen;
   an obturator sized and configured to pass through the inner lumen of the tube and to advance the clotted biological component through the tube to a distal end of the tube; and
   a cutting mechanism provided at the distal end of the tube to cut the clotted biological component, wherein the cutting mechanism is a blade having an outer surface about perpendicular to a longitudinal axis of the tube.

2. The device of claim 1, wherein the clotted biological component is a blood clot.

3. The device of claim 1, wherein the clotted biological component comprises a material selected from the group consisting of blood, autologous conditioned plasma, platelet-rich plasma, bone marrow aspirate, demineralized bone matrix, anticoagulants, clotting agents and growth factors.

4. The device of claim 1, wherein the tissue void is a bone void.

5. The device of claim 4, wherein the bone void is a tunnel, socket, opening or cavity.

6. The device of claim 1, wherein the device is configured to sequentially fill at least two tissue voids with material from the same clotted biological component.

7. The device of claim 1, wherein the cutting mechanism is a circular blade capable of being rotated relative to a longitudinal axis of the tube from a first, closed position to a second, open position, wherein in the second, open position the clotted biological component advances through the tube.

8. The device of claim 1, wherein the cutting mechanism is integral to the tube.

9. The device of claim 1, further comprising a matrix disposed within at least a part of the tube to allow formation of the clotted biological component on or within the matrix and subsequent transport and placement of the clotted biological component in the tissue void.

10. The device of claim 9, wherein the matrix is a flexible strand, a porous material, or a tape.

11. The device of claim 9, wherein the matrix is a suture strand securely attached to the tube.

12. The device of claim 1, wherein the clotted biological component further comprises collagen or allograft.

13. A method of providing a desired amount of a clotted biological component into an anatomical void formed in anatomical tissue, comprising the steps of
   providing a tube in the vicinity of the anatomical void, the tube having an inner lumen, a proximal end and a distal end, and a cutting mechanism at the distal end;
   forming a clotted biological component within the tube;
   advancing the clotted biological component towards the distal end of the tube so that at least a part of the clotted biological component exits the tube; and
   cutting off the at least part of the clotted biological component that exits the tube and filling the anatomical void by actuating a blade of the cutting mechanism from an open position to a closed position, wherein, when the blade is in the open position, the clotted biological component can pass through a most distal end of the tube and, when the blade is in the close position, an inner lumen of the tube is fully blocked so that the clotted biological component cannot pass through the most distal end of the tube.

14. The method of claim 13, wherein the at least part of the clotted biological component fully fills the anatomical void.

15. The method of claim 13, wherein the at least part of the clotted biological component partially fills the anatomical void.

16. The method of claim 13, wherein the anatomical void is a bone tunnel or socket.

17. The method of claim 13, further comprising the steps of:
   sealing the distal end of the tube with a distal cap;
   injecting at least one of blood and autologous conditioned plasma within the tube through the proximal end of the tube;
   optionally, providing a filler material within the tube and mixing the least one of blood and autologous conditioned plasma with the filler material to form the clotted biological component;
   removing the distal cap of the tube;
   placing the distal end of the tube over the anatomical void;
   advancing an obturator though the inner lumen of the tube and into the anatomical void, so that at least a part of the clotted biological component is advanced within the anatomical void;
   actuating a cutting or shearing mechanism located at the distal end of the tube, to cut the clotted biological component at a surface of the anatomical tissue and allow the at least part of the clotted biological component to fill in the anatomical void.

18. The method of claim 17, wherein the filler material is a stabilizing or a therapeutic material.

* * * * *